(12) United States Patent
Schleicher et al.

(10) Patent No.: US 10,732,270 B2
(45) Date of Patent: Aug. 4, 2020

(54) DRUG CARTRIDGE WITH ACOUSTIC REFLECTOR

(71) Applicant: Verily Life Sciences LLC, Mountain View, CA (US)

(72) Inventors: Brett Schleicher, San Francisco, CA (US); Benjamin Krasnow, Redwood City, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 363 days.

(21) Appl. No.: 15/887,700

(22) Filed: Feb. 2, 2018

(65) Prior Publication Data

US 2018/0259630 A1  Sep. 13, 2018

Related U.S. Application Data

(60) Provisional application No. 62/468,733, filed on Mar. 8, 2017.

(51) Int. Cl.
*G01S 7/521* (2006.01)
*G01S 15/02* (2006.01)
(Continued)

(52) U.S. Cl.
CPC ......... *G01S 7/521* (2013.01); *A61M 5/31568* (2013.01); *G01S 15/02* (2013.01);
(Continued)

(58) Field of Classification Search
CPC .......... G01S 7/521; G01S 15/02; G01S 15/08; A61M 5/31568; A61M 2205/8206;
(Continued)

(56) References Cited

U.S. PATENT DOCUMENTS

| 4,358,839 A | 11/1982 | Wittke |
| 5,311,871 A | 5/1994 | Yock |

(Continued)

FOREIGN PATENT DOCUMENTS

| WO | 2014/009442 A1 | 1/2014 | |
| WO | WO-2018164881 A1 * | 9/2018 | ............. G01S 15/02 |

OTHER PUBLICATIONS

International Search Report and Written Opinion from the International Searching Authority dated Jun. 8, 2017 for International Application No. PCT/US2017/017821, filed Feb. 14, 2017, 16 pages.

(Continued)

*Primary Examiner* — Daniel Pihulic
(74) *Attorney, Agent, or Firm* — Christensen O'Connor Johnson Kindness PLLC

(57) ABSTRACT

A drug cartridge to dispense an injectable fluid includes a drug cartridge body with an interior cavity, a neck region, and a bottom region. The neck region is opposite the bottom region and the interior cavity of the drug cartridge narrows in the neck region and is wider than most of the neck region in the bottom region. A transducer is coupled to emit sonic waves into the interior cavity towards the neck region, and the neck region is geometrically oriented to reflect the sonic waves back from the neck region towards the bottom region to be received by the transducer.

22 Claims, 4 Drawing Sheets

(51) Int. Cl.
  *G01F 23/296* (2006.01)
  *A61M 5/24* (2006.01)
  *A61M 5/315* (2006.01)
  *G01S 15/08* (2006.01)

(52) U.S. Cl.
  CPC ....... *A61M 5/24* (2013.01); *A61M 2205/3375* (2013.01); *A61M 2205/3379* (2013.01); *A61M 2205/3561* (2013.01); *A61M 2205/3569* (2013.01); *A61M 2205/50* (2013.01); *A61M 2205/702* (2013.01); *A61M 2205/8206* (2013.01); *G01F 23/296* (2013.01); *G01S 15/08* (2013.01)

(58) Field of Classification Search
  CPC ...... A61M 2205/3561; A61M 2205/50; A61M 2205/3379; A61M 2205/3569; A61M 2205/3375; A61M 2205/702; A61M 5/24; G01F 23/296
  See application file for complete search history.

(56) References Cited

U.S. PATENT DOCUMENTS

| | | |
|---|---|---|
| 5,678,189 A | 10/1997 | Barnes |
| 5,728,074 A | 3/1998 | Castellano et al. |
| 5,826,066 A | 10/1998 | Jardine et al. |
| 6,585,698 B1 | 7/2003 | Packman et al. |
| 7,927,281 B2 | 4/2011 | Wheeler |
| 8,226,599 B2 | 7/2012 | Engle |
| 8,556,866 B2 | 10/2013 | Krulevitch et al. |
| 8,560,271 B2 | 10/2013 | Koehler et al. |
| 8,817,258 B2 | 8/2014 | Whalley et al. |
| 9,008,764 B2 | 4/2015 | Larsen |
| 9,101,723 B2 | 8/2015 | Larsen |
| 9,250,111 B2 | 2/2016 | Whalley et al. |
| 9,255,830 B2 | 2/2016 | Whalley et al. |
| 2005/0209601 A1 | 9/2005 | Bowman et al. |
| 2008/0188813 A1 | 8/2008 | Miller et al. |
| 2008/0243088 A1 | 10/2008 | Evans |
| 2009/0043253 A1 | 2/2009 | Podaima |
| 2009/0069742 A1 | 3/2009 | Larsen |
| 2011/0009824 A1 | 1/2011 | Yodfat et al. |
| 2011/0313395 A1 | 12/2011 | Krulevitch et al. |
| 2012/0101451 A1 | 4/2012 | Boit et al. |
| 2012/0302849 A1 | 11/2012 | Grant et al. |
| 2013/0116666 A1 | 5/2013 | Shih et al. |
| 2013/0310756 A1 | 11/2013 | Whalley et al. |
| 2014/0249410 A1 | 9/2014 | Uber et al. |
| 2014/0379874 A1 | 12/2014 | Starr et al. |
| 2015/0112316 A1 | 4/2015 | Cudak et al. |
| 2015/0174342 A1 | 6/2015 | Mitrosky et al. |
| 2015/0209510 A1 | 7/2015 | Burkholz et al. |
| 2016/0022539 A1 | 1/2016 | Daines |
| 2016/0030683 A1 | 2/2016 | Taylor et al. |
| 2016/0074587 A1 | 3/2016 | Searle et al. |
| 2018/0259630 A1* | 9/2018 | Schleicher ........ A61M 5/31568 |
| 2018/0333540 A1* | 11/2018 | Wendland ............... A61M 5/20 |
| 2019/0262543 A1* | 8/2019 | Reich ................ A61M 5/31525 |
| 2019/0321559 A1* | 10/2019 | Sheridan ........... A61M 5/31528 |

OTHER PUBLICATIONS

International Search Report and Written Opinion dated May 14, 2018 from the International Searching Authority for International Application No. PCT/US2018/019917, filed Feb. 27, 2018, 30 pages.

* cited by examiner

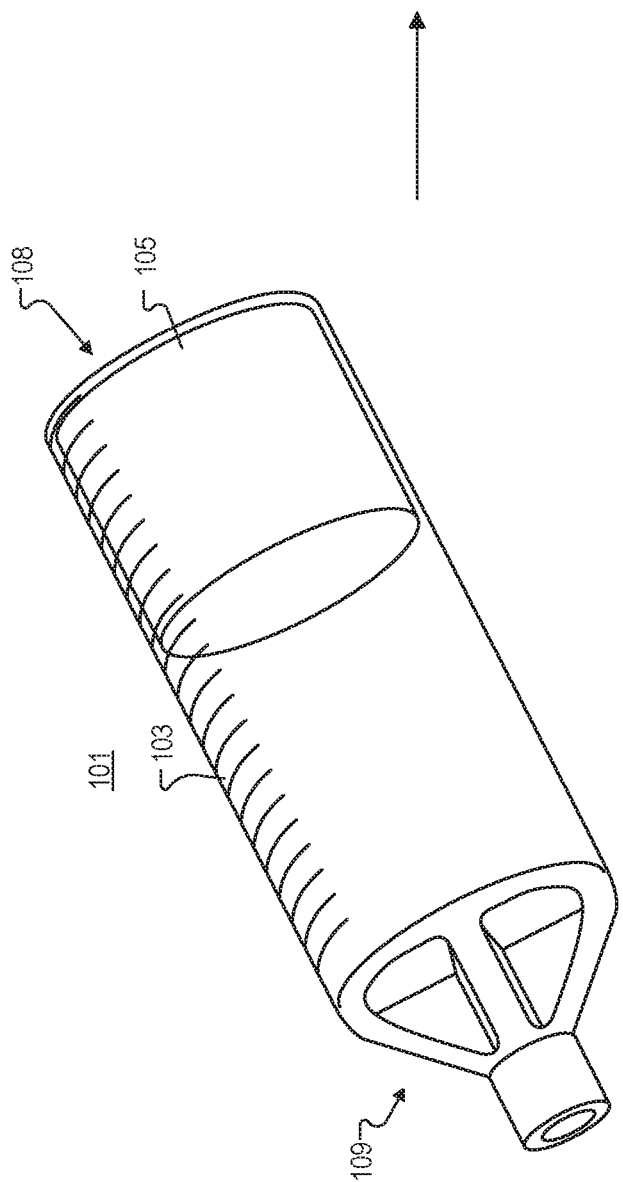
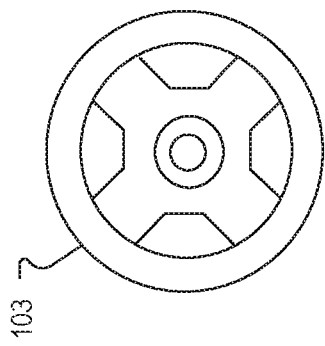
FIG. 1L
FIG. 1M

DRUG CARTRIDGE WITH ACOUSTIC REFLECTOR

RELATED APPLICATIONS

This application claims the benefit of U.S. Provisional Application No. 62/468,733, filed Mar. 8, 2017, which is incorporated by reference in its entirety.

TECHNICAL FIELD

This disclosure relates generally to drug injection and in particular but not exclusively, relates to tracking injection quantities.

BACKGROUND INFORMATION

Measuring the quantity and recording the timing of a drug's administration is an integral part of many disease treatments. For many treatments, to achieve the best therapeutic effect, specific quantities of a drug may need to be injected at specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range.

Currently, there are a limited number of methods or devices capable of tracking drug administration without requiring the user to manually measure and record the volume, date, and time. A variety of glucose injection syringes/pens have been developed, but there is much room for significant advancement in the technology in order to reduce the size, lower the cost, enhance the functionality, and improve the accuracy. Thus, the current technology may not be an ideal long-term solution. For example, current insulin pens are often disposable, but do not include dosage tracking. A smaller portion of the market is composed of reusable pens which are more expensive, and still do not include accurate dosage-tracking capabilities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

FIGS. 1A-1M illustrate a variety of drug cartridge configurations, in accordance with several embodiments of the disclosure.

DETAILED DESCRIPTION

Figure 1A:
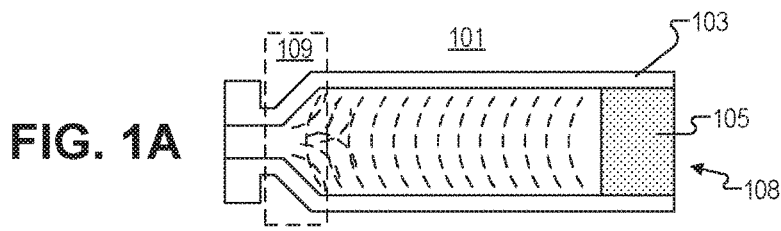

Embodiments of an apparatus and method for a drug cartridge with an acoustic reflector are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Drug cartridges may be used in insulin pens to dispense insulin into a user. When the user needs to inject insulin, the user may put a drug cartridge in an insulin pen and inject themselves with a desired dose of insulin. However, with conventional pens/cartridges it is difficult to track the dose injected over time, since the user would manually have to record time, dosage amount, etc. Here a method and system for automated tracking is disclosed.

The geometry of the drug cartridge is an important factor in dose volume measurement systems that incorporate ultrasonic rangefinding to determine the volume of fluid in the drug cartridge. The return echo in ultrasonic rangefinding, which is reflected off of the cartridge geometry, can be reflected and dispersed which decreases the accuracy and efficiency of the ultrasonic sensor. In cartridges with sub-optimal geometry, less of the sensor's transmitted energy is returned to the sensor receiver when a portion of the ultrasonic wave is lost because of undesirable reflections. Standard drug cartridges can be improved by the incorporation of geometries that optimize ultrasonic reflection. This disclosure describes systems/methods to incorporate a suitable ultrasonic reflector that optimizes the acoustic echo, enabling an accurate ultrasonic measurement sensor.

FIGS. 1A-1M illustrate a variety of drug cartridge 101 configurations, in accordance with several embodiments of the disclosure. It is worth noting that all embodiments depicted include drug cartridge body 103 (likely made from borosilicate glass or the like), stopper 105, and neck region 109. To dispense fluid from neck region 109, stopper 105 is pushed into body 103, thus expelling fluid from neck region 109. Although depicted in more detail in FIG. 2, stopper 105 includes a transducer to emit sonic waves into the interior cavity of drug cartridge 101, and the waves are reflected back from neck region 109. More specifically, the waves travel from stopper 105 along the length of drug cartridge 101 to neck region 109; neck region 109 reflects the waves, and the waves once again travel along the length of drug cartridge 101 back to the transducer in stopper 105. The reflected signal may be used to determine the volume of liquid in drug cartridge 101 and how much liquid was dispensed. One of skill in the art will appreciate that "transducer" may include more than one device (e.g., one device to emit waves, and one device to receive waves). As depicted, neck region 109 is opposite bottom region 108 (where stopper 105 is initially located before being pushed in), and the interior cavity of drug cartridge 101 is narrows proximate to neck region 109 and is wider than most of neck region 109 in bottom region 108. In other words, bottom region 108 is wider than most of neck region 109. In all embodiments, neck region 109 is geometrically oriented to reflect the sonic waves back from neck region 109 towards bottom region 108 to be received by the transducer in stopper 105.

FIG. 1A shows an embodiment, where the neck region 109 narrows from the wider body 103 of drug cartridge 101 at approximately a 45° angle. As shown, this may result in the sonic waves being reflect from neck region 109 back into body 103 at approximately 45° angles.

Figure 1B:
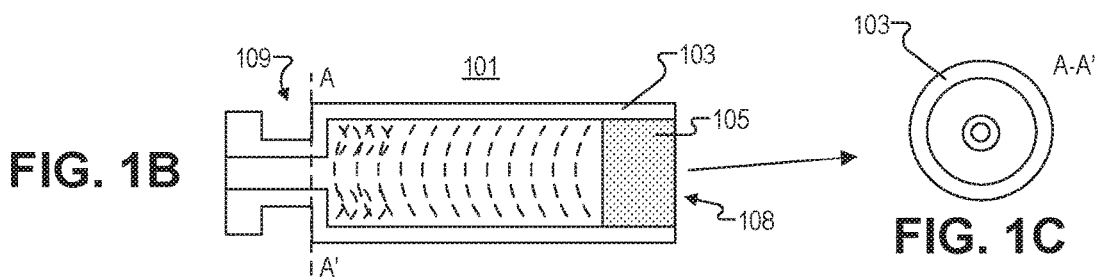

FIG. 1B depicts a modified shoulder angle in neck region 109 of drug cartridge 101. Rather than drawing the shoulder of drug cartridge 101 to an acute angle, the cartridge shoulder is formed at substantially 90° degrees from the long axis of the cartridge body 103, thereby producing a ledge. Cartridges are often formed by heating and drawing a glass tube. A shaped tool is pressed to the heated glass which draws and forms the shoulder and neck geometry. A drug cartridge with a 90 degree neck can be created using the same processes. This neck region 109 is at substantially a 90° angle (orthogonal) to the direction of sonic wave emission/travel. This 90° neck region 109 may provide enhanced reflection capabilities by reflecting the sonic waves at the same angle as they are emitted from the transducer (in stopper 105). This may allow stopper 105 to receive more waves with less interference (reflections from side walls), thereby providing an improved signal-to-noise ratio for drug cartridge 101. Similarly, more waves may be bounced directly back to the transducer, enhancing signal strength. One of ordinary skill will appreciate that this increase in signal strength and decrease in attenuation applies to all the embodiments depicted.

Figure 1C:
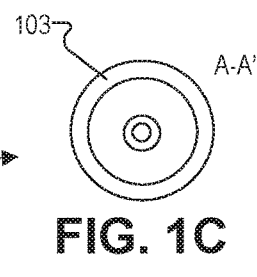

FIG. 1C shows one embodiment of a face-on view of drug cartridge 101 from FIG. 1B as cut along line A-A'. As shown, the 90° angle neck region 109 is uniform around the entire neck region 109. In other words, there are no tapered portions of neck region 109 because neck region 109 is indented all the way around drug cartridge 101.

Figure 1D:
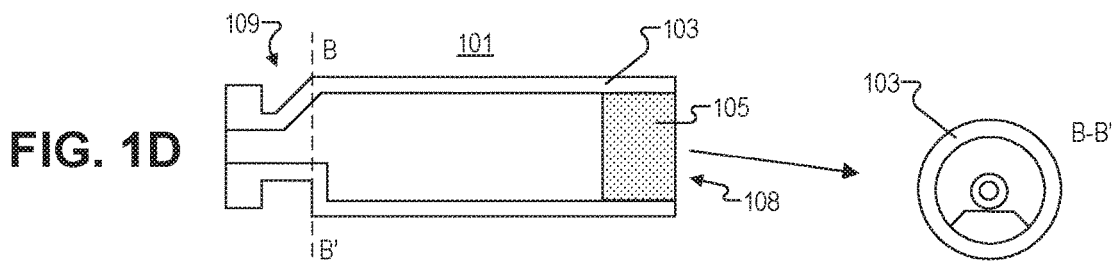

FIG. 1D depicts a similar drug cartridge 101 as those depicted in FIGS. 1B and 1C, in that it has a ledge formed at 90° degrees from the long axis of cartridge body 103. However, one major difference is that the shoulder of drug cartridge 101 does not extend all the way around drug cartridge body 103. In fact, neck region 109 includes a single indentation that occupies approximately 20-50% of neck region 109. Rather than indenting the entire shoulder of drug cartridge 101 to form a reflective surface, localized areas of neck region 109 may be indented to form a reflector. Existing injection devices that use cartridges are designed to accept cartridges that typically have an angle to the shoulder (e.g., 45° similar to FIG. 1A). Change to the shoulder geometry may make the cartridge incompatible with existing injection devices. An advantage of the shoulder indent is that the cartridge generally retains the tapered shoulder and therefore will be compatible with the receptacle of existing devices. These indentations could be sonically aligned with the location of the ultrasonic transducer in stopper 105 to minimize the size of the transducer or focus the beam directly onto these indentations.

Figure 1E:
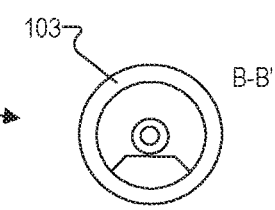

FIG. 1E depicts one embodiment of a face-on view of drug cartridge 101 from FIG. 1D as cut along line B-B'. As shown, the shoulder/indent in neck region 109 is only formed in part of neck region 109, so that a first portion of neck region 109 has a tapered narrowing, but the shoulder has right-angle narrowing.

Figure 1F:
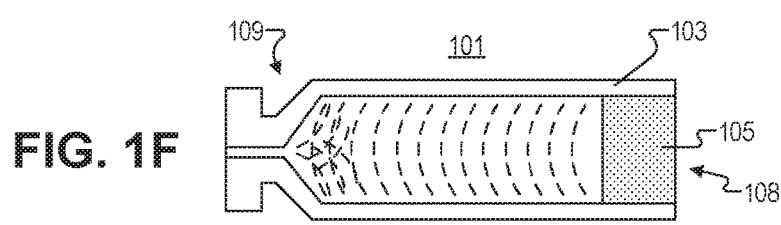

FIG. 1F illustrates a drug cartridge 101 that is similar in many ways to the drug cartridge of FIG. 1A, in that the exterior of body 103 has the same (or a substantially similar) profile as the drug cartridge of FIG. 1A. However, cartridge 101 of FIG. 1F has a narrower opening in neck region 109, but the increased surface area of neck region 109 provides enhanced reflection. This may improve the quantity of sonic waves received by the transducer disposed in stopper 105. In one embodiment, the inner walls of body 103 in neck region 109 may have an angle greater than 45° relative to body 103. For example, neck region 109 may have an angle of 50-90°.

Figure 1G:
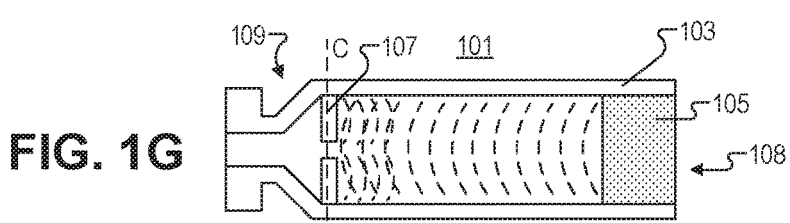

FIG. 1G shows a drug cartridge 101 that is similar in many ways to the drug cartridge of FIG. 1A, but drug cartridge 101 in FIG. 1G has reflecting insert 107 disposed in neck region 109. Reflecting insert 107 is disposed to reflect the sonic waves emitted from the transducer. In the depicted embodiment, at least one hole is disposed in reflecting insert 107 to permit passage of the injectable fluid through neck region 109. In some embodiments, reflecting insert 107 may be constructed from similar materials as the cartridge (e.g., borosilicate glass) or other materials that serve as a suitable reflector such as metals, ceramics, and rigid plastic. The material can be selected to optimize reflection of the ultrasonic wave and be suitable for drug stability and compatibility. In some embodiments, reflecting insert 107 may be located as close to neck region 109 as possible to maximize the total amount of useable volume of drug cartridge 101. Reflecting insert 107 may be located at the transition from the cylindrical body 103 to the conical neck region 109 of drug cartridge 101. Smaller diameter reflectors could alternatively be positioned inside neck region 109 to further maximize useable volume, and increase the distance between sensor (which will advance towards neck region 109 during use) and disc. While the embodiments depicted show a cylindrical drug cartridge 101, one of ordinary skill in the art will appreciate that other shapes may be used such as square, hexagonal or the like.

Reflecting insert 107 may have one or more perforations to allow fluid to pass through from the cylindrical portion of drug cartridge 101 to neck region 109 where the outlet of drug cartridge 101 is located. Furthermore, reflecting insert 107 may fabricated from fritted glass, which has many porous channels to allow fluid to pass. These perforations can be located where they minimize their interference of the ultrasonic signal. For example, they can be located at the center of reflecting insert 107, around the perimeter, or distributed throughout. A target area on the disc without perforations may be considered to optimize the reflection. Lastly, holes/perforations may be used to create turbulence and promote mixing of injectable fluids, in accordance with the teachings of the present disclosure.

Figures 1H, 1I, 1J, 1K:
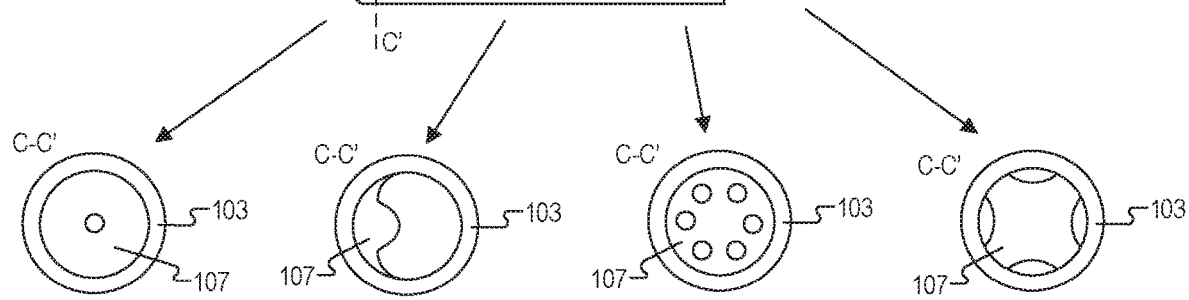

FIG. 1H is one possible embodiment of a reflecting insert 107 from FIG. 1G as cut along line C-C'. As illustrated a small circular hole is disposed in the center of reflecting insert 107. As shown, reflecting insert 107 is circular and may be adhered to the inside of body 103 with a pressure fit, adhesive, or the like. In the depicted embodiment, the transducer may be positioned to primarily reflect off of the portion of reflecting insert 107 that does not have a hole.

FIG. 1I is one possible embodiment of a reflecting insert 107 from FIG. 1G as cut along line C-C'. In the depicted embodiment, reflecting insert 107 is substantially crescent shaped with a rounded section that extends outward from a convex interior edge. In the depicted embodiment, the transducer may be positioned to primarily reflect off of the rounded section that extends outward from the convex interior edge. This low-profile reflecting insert 107 could allow fluid to easily flow out of drug cartridge 101 since less space in neck region 209 is occupied by reflecting insert 107.

FIG. 1J is one possible embodiment of a reflecting insert 107 from FIG. 1G as cut along line C-C'. In the depicted embodiment, reflecting insert 107 includes a plurality of holes disposed proximate to edges of reflecting insert 107. More specifically, reflecting insert 107 has six holes through it with the holes evenly spaced in a hexagonal shape. In other embodiments, other numbers of holes may extend through reflecting insert 107. For example, two, three, four, five, seven, or eight hole configurations may all be used; these configurations may have even spacing or uneven spacing, in accordance with the teachings of the present disclosure. In the depicted embodiment, the transducer may be positioned to primarily reflect off the center of reflecting insert 107 where there are no holes.

FIG. 1K is one possible embodiment of a reflecting insert 107 from FIG. 1G as cut along line C-C'. In the depicted embodiment, reflecting insert 107 includes a circular disk, with one or more edges of the circular disk removed to permit passage of the injectable fluid into neck region 109. In the depicted embodiment, four lens-shaped regions have been removed from the edges of the circular disk. However, in different embodiments other uniquely shaped regions may be removed from the edges of reflecting insert 107. Moreover, there may be any number of these cut-outs in reflecting insert 107. In the depicted embodiment, the transducer may be positioned to primarily reflect off the center of reflecting insert 107 where there are no holes.

FIG. 1L illustrates a perspective view of an example drug cartridge 101 with indentations in the neck region 109 (similar to FIG. 1D but there are four evenly spaced indentations around the neck). As depicted these indentations may have a 90° angle relative to the body 103 of drug cartridge 101. These indentations in drug cartridge body 103 reflect the sonic waves and are, at least in part, oriented perpendicular to the direction of travel of the sonic waves. In the depicted embodiment, the transducer may be positioned to primarily reflect off the indentations to avoid unnecessary scattering. In other embodiments, the transducer may just emit sonic waves towards neck region 109 and the indentations simply provide a larger flat area for backscattering (to increase the strength of the signal).

FIG. 1M is a face-on illustration of drug cartridge 101 from FIG. 1L. As shown, the indentations are evenly spaced around neck region 109, and leave un-indented portions between them (which extend towards the opening in neck region 109 at ~45° from the body 103).

Figure 2:
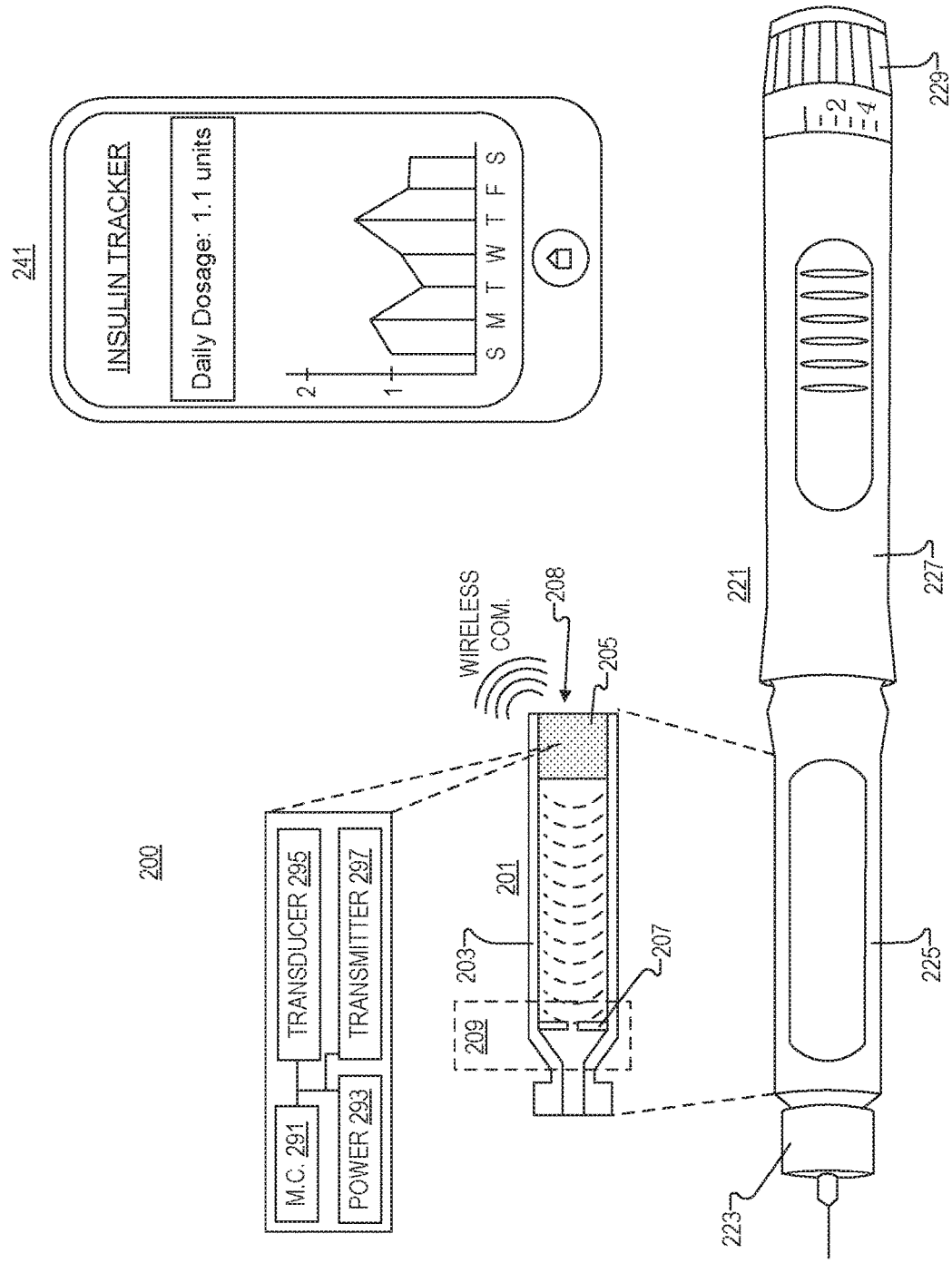
FIG. 2 illustrates a system for fluid injection and tracking, in accordance with an embodiment of the disclosure.

FIG. 2 illustrates a system 200 for fluid injection and tracking, in accordance with an embodiment of the disclosure. System 200 includes drug cartridge 201, injection pen 221, and processing device 241 (e.g., a smart phone).

Like the embodiments depicted in FIG. 1A-1L drug cartridge 201 includes cartridge body 203, stopper 205, neck region 209, and (optionally) reflecting insert 207. One of ordinary skill in the art will appreciate that drug cartridge 201 may take the form of any cartridge in FIGS. 1A-1L, and others not depicted, in accordance with the teachings of the present disclosure.

In the depicted embodiment, stopper 205 is adapted to fit within the interior cavity of drug cartridge body 203, and stopper 205 includes transducer 295, microcontroller 291, power supply 293, and transmitter 297. Microcontroller 291 is coupled to transducer 295, such that in response to a control signal from microcontroller 291, transducer 295 emits sonic waves into the interior cavity of drug cartridge 201. Power supply 293 is coupled to microcontroller 291 to power microcontroller 291. Wireless (or, in other embodiments, wired) transmitter 297 may be coupled to microcontroller 291, such that in response to sonic waves being reflected back to stopper 205, microcontroller 291 calculates an amount of liquid in drug cartridge 201 and wireless transmitter 297 transmits data (including information about the amount of liquid in drug cartridge 201) to processing device 241.

Injection pen 221 is a hand-held device and includes needle 223, chamber 225 (to hold drug cartridge 201), body 227 (including a drug dispensing actuator to push in stopper 205 and extract fluid from drug cartridge 201), and a drug delivery control switch 229 (twist the switch to control the dosage). However, as one of ordinary skill in the art will appreciate, injection pen 221 can take other configurations and have other components. It is appreciated that injection pen 221 may be a generic store-bought pen, and drug cartridge 201 is configured to fit in most generic pens.

Processing device 241 (e.g., a smartphone, tablet, general purpose computer, distributed system, servers connect to the internet, or the like) may be coupled to receive data from drug cartridge 201 to store/analyze this data. For instance, in the depicted embodiment, processing device 241 is a smartphone, and the smartphone has an application running recording how much insulin has been spent from pen 221. Moreover the application is plotting how much insulin has been deposited by the user over the past week. This information may have been received directly from microcontroller 291/transmitter 297, or may have been acquired from pen 221 if pen 221 includes signal amplification circuitry or a direct plug-in (micro USB port or the like). One of ordinary skill in the art will appreciate that there are many ways processing device 241 can parse the injection data and electrically couple to drug cartridge 201, in accordance with the teachings of the present invention.

Figure 3:
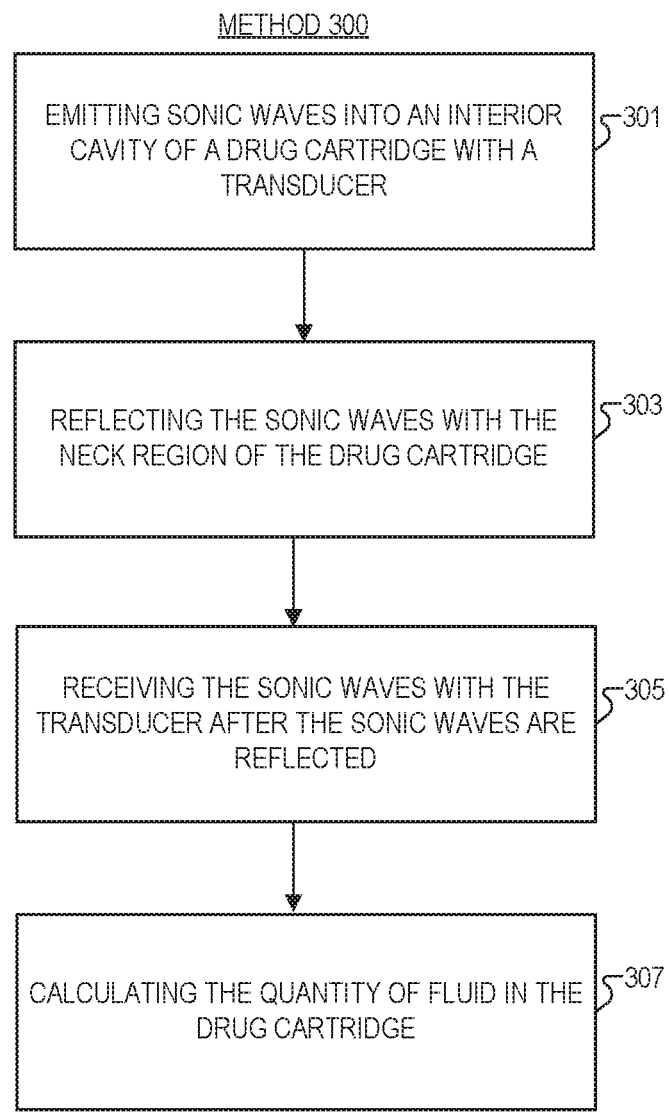
FIG. 3 is a flow chart illustrating a method of monitoring a quantity of fluid in a drug cartridge, in accordance with several embodiments of the disclosure.

FIG. 3 is a flow chart illustrating a method 300 of monitoring a quantity of fluid in a drug cartridge, in accordance with several embodiments of the disclosure. The order in which some or all of process blocks 301-307 appear in method 300 should not be deemed limiting. Rather, one of ordinary skill in the art having the benefit of the present disclosure will understand that some of method 300 may be executed in a variety of orders not illustrated, or even in parallel. Further, blocks may be added or removed in accordance with the teaching of the present disclosure.

Block 301 shows emitting sonic waves into an interior cavity of a drug cartridge (see e.g., FIG. 1A-1L) with a transducer. The sonic waves travel from the transducer towards a neck region of the drug cartridge, which is opposite a bottom region of the drug cartridge. The interior cavity is narrower proximate to the neck region (through which the fluid is dispensable) and wider proximate to the bottom region.

Block 303 illustrates reflecting the sonic waves with the neck region. The neck region is geometrically oriented to reflect the sonic waves back from the neck region towards the bottom region to be received by the transducer. In one embodiment, this may include reflecting the sonic waves using one or more indentations disposed in the neck region of the drug cartridge. In some embodiments, the one or more indentations include a surface that is substantially orthogonal to a direction of emission of the sonic waves from the transducer. In another or the same embodiment, reflecting the sonic waves includes using a reflecting insert disposed in the neck region of the drug cartridge. The reflecting insert may include one or more holes disposed in it to permit passage of the fluid into the neck region.

Block 305 depicts receiving the sonic waves with the transducer after the sonic waves are reflected. The transducer is coupled to a microcontroller which may control emission and data collection associated with the sonic waves. For example, the microcontroller may record every time a wave of a particular intensity is incident on the transducer. The microcontroller may be coupled to a transmitter to send this information to a third party device.

Block 307 shows calculating, with the microcontroller, the quantity of fluid in the drug cartridge in response to the transducer receiving the sonic waves.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A drug cartridge to dispense an injectable fluid, comprising:
    a drug cartridge body with an interior cavity, a neck region, and a bottom region, wherein the neck region is opposite the bottom region, and the interior cavity of the drug cartridge narrows in the neck region and is wider than most of the neck region in the bottom region; and
    a transducer coupled to emit sonic waves into the interior cavity towards the neck region, wherein the neck region is geometrically oriented to reflect the sonic waves back from the neck region towards the bottom region to be received by the transducer.

2. The drug cartridge of claim 1, further comprising a stopper adapted to fit within the interior cavity of the drug cartridge body, wherein the stopper includes:
    the transducer; and
    a microcontroller coupled to the transducer, wherein in response to a control signal form the microcontroller the transducer emits the sonic waves.

3. The drug cartridge of claim 2, wherein the neck region includes a reflecting insert disposed to reflect the sonic waves, and wherein at least one hole is disposed in the reflecting insert to permit passage of the injectable fluid through the neck region.

4. The drug cartridge of claim 3, wherein the reflecting insert includes a plurality of holes disposed proximate to edges of the reflecting insert.

5. The drug cartridge of claim 3, wherein the reflecting insert is substantially crescent shaped with a rounded section that extends outward from a convex interior edge.

6. The drug cartridge of claim 3, wherein the reflecting insert includes a circular disk, wherein one or more edges of the circular disk are removed to permit the passage of the injectable fluid into the neck region.

7. The drug cartridge of claim 2, wherein the neck region includes one or more indentations in the drug cartridge body to reflect the sonic waves.

8. The drug cartridge of claim 7, wherein the neck region includes a single indentation to form a ledge in the drug cartridge.

9. The drug cartridge of claim 7, wherein the neck region includes four indentations evenly spaced around the neck region.

10. The drug cartridge of claim 2, wherein the stopper further comprises:
    a power supply coupled to the microcontroller to power the microcontroller; and
    a wireless transmitter coupled to the microcontroller, wherein in response to the sonic waves reflecting back to the stopper, the microcontroller calculates an amount of liquid in the drug cartridge, and the wireless transmitter is coupled to the microcontroller to transmit data including information about the amount of liquid.

11. A system for fluid injection, comprising:
    a hand-held housing including a chamber configured to receive a drug cartridge, wherein the hand-held housing includes an actuator configured to push the fluid from the drug cartridge;
    the drug cartridge, including:
        an interior cavity;
        a neck region;
        a bottom region opposite the neck region, wherein the interior cavity of the drug cartridge narrows in the neck region;
        a stopper disposed in the bottom region; and
        a transducer disposed in the stopper and coupled to emit sonic waves into the interior cavity towards the neck region, wherein the neck region is geometrically oriented to reflect the sonic waves back from the neck region towards the bottom region to be received by the transducer.

12. The system of claim 11, wherein the neck region includes one or more indentations in the drug cartridge to reflect the sonic waves.

13. The system of claim 12, wherein the one or more indentations include two or more indentations disposed symmetrically around the neck region, and wherein the one or more indentations include a reflecting surface that is substantially orthogonal to a direction of travel of the sonic waves.

14. The system of claim 11, wherein the neck region includes a reflecting insert with at least one hole disposed in the reflecting insert.

15. The system of claim 14, wherein the reflecting insert is circular and includes a plurality of holes disposed proximate to edges of the reflecting insert to permit passage of the fluid into the neck region.

16. The system of claim 14, wherein the reflecting insert is substantially crescent shaped with a section that extends outward from a convex interior edge.

17. The system of claim 14, wherein the reflecting insert includes a circular disk, wherein one or more edges of the circular disk are removed to permit passage of the fluid into the neck region.

18. A method of monitoring a quantity of fluid in a drug cartridge, comprising:
- emitting sonic waves into an interior cavity of the drug cartridge with a transducer, wherein the sonic waves travel from the transducer towards a neck region of the drug cartridge which is opposite a bottom region of the drug cartridge, and wherein the interior cavity narrows proximate to the neck region through which the fluid is dispensable;
- reflecting the sonic waves with the neck region, wherein the neck region is geometrically oriented to reflect the sonic waves back from the neck region towards the bottom region to be received by the transducer; and
- receiving the sonic waves with the transducer after the sonic waves are reflected, wherein the transducer is coupled to a microcontroller; and
- calculating, with the microcontroller, the quantity of fluid in the drug cartridge in response to the transducer receiving the sonic waves.

19. The method of claim 18, wherein reflecting the sonic waves includes using one or more indentations disposed in the neck region of the drug cartridge to reflect the sonic waves.

20. The method of claim 19, wherein the one or more indentations include a surface that is substantially orthogonal to a direction of emission of the sonic waves from the transducer.

21. The method of claim 18, wherein reflecting the sonic waves includes using a reflecting insert disposed in the neck region of the drug cartridge to reflect the sonic waves.

22. The method of claim 21, wherein the reflecting insert includes one or more holes disposed in the reflecting insert to permit passage of the fluid into the neck region.

* * * * *